US006558703B1

(12) United States Patent
Karlsson et al.

(10) Patent No.: US 6,558,703 B1
(45) Date of Patent: May 6, 2003

(54) POROUS HYDROXYAPATITE PARTICLES AS CARRIERS FOR DRUG SUBSTANCES

(75) Inventors: Christer Karlsson, Lindome (SE); Per Johan Lundberg, Mölndal (SE); Adam Rosinski, Göteborg (SE); Malin Söderbom, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/214,318

(22) PCT Filed: Nov. 18, 1998

(86) PCT No.: PCT/SE98/02089

§ 371 (c)(1),
(2), (4) Date: Jan. 4, 1999

(87) PCT Pub. No.: WO99/27912

PCT Pub. Date: Jun. 10, 1999

(30) Foreign Application Priority Data

Nov. 28, 1997 (SE) ................................................ 9704400

(51) Int. Cl.[7] ................................................ A61K 9/14
(52) U.S. Cl. ........................ 424/489; 424/490; 424/464; 424/484; 424/469; 424/470
(58) Field of Search ................................. 424/489, 464, 424/490, 484, 469, 470

(56) References Cited

U.S. PATENT DOCUMENTS 5,149,523 A * 9/1992 Lundberg et al.
5,443,459 A * 8/1995 Wong et al. ............. 604/892.1
5,834,496 A * 11/1998 Young
5,876,446 A * 3/1999 Agrawal et al. ............. 623/11
6,099,849 A * 8/2000 Mansouri

FOREIGN PATENT DOCUMENTS

| EP | 0163178 | 12/1985 |
|----|---------|---------|
| EP | 0294206 | 12/1988 |
| EP | 0376331 | 7/1990 |
| WO | WO 92/12714 | * 6/1992 |

OTHER PUBLICATIONS

Biomed. Sci. Instrum. (1994), 30, 169–74 (Abstract).
Biomed Mater. Eng. (1994), 4(4), 283–90 (Abstract).
J. Biomed. Mater. Res. (1996), Feb., 30(2), 321–8.
Biomaterials (1996), Oct., 17(20), 1959–64.
Biomaterials (1997), Nov., 18(21), 1433–9.
Biomed. Sci. Instrum. (1997), 34, 59–64 (Abstract).
Biomed. sci. Instrum. (1997), 34, 13–17 (Abstract).

* cited by examiner

Primary Examiner—Thurman K. Page
Assistant Examiner—Amy E Pulliam
(74) Attorney, Agent, or Firm—White & Case LLP

(57) ABSTRACT

A drug delivery system for oral administration in solid dry form of a greasy/oily/sticky substance and a pharmaceutically active substance or a pharmaceutically active substance which itself is greasy/oily/sticky characterized by having a plurality of porous inorganic particles of small size incorporated with considerable amounts of greasy/oily/sticky substances and having fast release characteristics and a process for the preparation of such porous inorganic particles containing greasy/oily/sticky substances.

12 Claims, No Drawings

POROUS HYDROXYAPATITE PARTICLES AS CARRIERS FOR DRUG SUBSTANCES

FIELD OF THE INVENTION

The present invention is related to a new oral pharmaceutical dosage form comprising porous inorganic particles incorporated with considerable amounts of greasy, oily or sticky (greasy/oily/sticky) substances where the new dosage form is characterised by being dry and easy to handle and having fast release properties.

BACKGROUND OF THE INVENTION

In many thereapeutic areas the need for incorporating absorption enhancers (e.g. glycerol esters for increased absorption of heparin or heparin fragments or derivatives as described in WO 95/00152 to Pharmacia), solubilizing agents (like polyethoxylated hydrogenated castor oils for felodipine as disclosed in EP 0249587 to AB Hässle), suspending agents (e.g. soybean oil or fractionated coconut oil for 1,2,4-benzotriazine oxide as disclosed in U.S. Pat. No. 5,597,582 to Sanofi), or the like into the dosage forms for drug delivery has arisen.

Incorporation of larger amounts of greasy, oily or sticky substances into pharmaceutical dosage forms have since long been known to cause technical problems. One of the problems has been to get pharmaceutically acceptable dry materials that are easy to handle and use as such or to use in later processing steps.

Earlier ways to circumvent the problem include filling the greasy/oily/sticky substances as such into soft gelatin capsules, as for instance described in U.S. Pat. No. 5,589,455 (Han Mi Pharm) where a concentrate for soft gelatin capsule filling comprising a cyclosporin and an oil component (improving bioavailability) is disclosed.

Many researchers have during the years described the advantage of using many small pellets (multiple unit) as a dosage form, with respect to their behaviour in vivo, i.e. especially with respect to their gastric emptying properties, see for instance Bogentoft et al, J. Clin. Pharmacol. 1978, 14, 351–5.

Another way to circumvent the problem, in line with the above findings, is to use microencapsulation. This method is, however, expensive as it includes many steps and is also often associated with big scaling-up troubles. The method has been described e.g by Luzzi in J.Pharm.Sci,1970,59,(10),1367–76.

1. Prior Art

WO 94/23703 (Kabi Pharmacia AB) discloses the manufacture of porous cellulose matrices and a multiple unit preparation containing a bioactive substance comprising porous cellulose matrice particles. However, this reference neither pertains to the problem of handling greasy, oily or sticky substances nor does it pertain to inorganic matrices.

EP 294 206 (Unilever NV) discloses porous spheroidal silica having certain characteristics having up to 50% by weight of the $SiO_2$ of included material such for example therapeutic agents. However, this reference neither pertains to the problem of handling greasy, oily or sticky substances nor does it show any achievement of fast release properties.

2. Description of the Invention

It has now been found that a drug delivery system for oral administration in solid dry form of greasy, oily or sticky substance(s) and pharmaceutically active substance(s) or pharmaceutically active substance(s) which itself/themselves is/are greasy, oily or sticky characterized by having porous inorganic particles of small size incorporated with considerable amounts of greasy, oily or sticky substances and having fast release characteristics can overcome the drawbacks associated with previous techniques.

Thus, the present invention provides a new dosage form principle for incorporation of greasy, oily or sticky materials into particles of small size, thus enabling a possibility to make multiple unit systems thereof. To achieve this, it has been found that highly porous inorganic particles are beneficial to use.

One characteristic of the present invention is the small size of the porous particles. The size is between 5 to 150 μm, preferably 20 to 100 μm.

Another characteristic of the present invention is the considerable amount of the greasy, oily or sticky substance. By considerable amount in this specification is meant 15% w/w to 40% w/w, preferably 20% w/w to 40% w/w, most preferably 30% w/w to 40% w/w.

The greasy, oily or sticky substances incorporated may be, but are not restricted to, pharmaceutically active substances, such as almokalant or vitamin A; pharmaceutically active substances which are themselves not greasy, oily or sticky but which together with a greasy, oily or sticky substance is especially suitable to be incorporated into the formulation are such as felodipine, melagatran, or inogatran; absorption enhancers which are greasy, oily or sticky and selected among mono-, di- or triglycerides or mixtures thereof, such as Akoline® MCM, Imvitor 308, Imvitor 742, Imvitor 928, Imvitor 988, glycerol de caprylate®; solubilizers, such as semi-solid or liquid non-ionic surface active agents, for example such containing polyethyleneglycols as esters or ethers, and which are chosen from polyethoxylated fatty acids, hydroxylated fatty acids and fatty alcohols and especially chosen from the group polyethoxylated castor oil, polyoxyethylenated hydrogenated castor oils (Cremophors), polyethoxylated fatty acid from castor oil or polyethoxylated fatty acid from hydrogenated castor oil and are known under the trade names such as Cremophor®, Myrj, Polyoxol 40 stearate, Emerest 2675, Lipal 395 and HCO 50.

The drug delivery system according to the invention is also characterized by having fast release characteristics when they with an in vitro dissolution test release not less than 60% (preferably 70% w/w) of pharmaceutically active substance and greasy/oily/sticky substances, or drug when the drug is the greasy, oily or sticky substance, within 30 minutes or shorter.

For the greasy, oily or sticky substances the dissolution rate is determined using USP apparatus No. 2 (paddle), operated at 100 rpm. The dissolution medium has a temperature of 37° C. Further there is a demand on the amount and art of dissolution medium, that it enables for the whole dose to be tested a non-retarded homogeneous distribution of liberated greasy, oily or sticky substance within the medium.

For the specific greasy, oily or sticky substances shown in the examples, the medium disclosed in each example is the appropriate one.

For the drug substances the dissolution rate is determined using USP apparatus No. 2 (paddle), operated at 100 rpm. The dissolution medium has a temperature of 37° C. Further there is a demand on the amount and art of dissolution medium, that it enables for the whole dose to be tested, a non-retarded homogenous distribution of liberated drug within the medium (sink conditions).

For the specific drugs shown in the examples, the medium disclosed in each example is the appropriate one.

It should be noted that for the one and same formulation different dissolution media might be chosen depending on the properties of the substances to be tested, if there are a greasy, oily or sticky substance and a pharmaceutically active substance present in the formulation, depending on which one of these that are to be tested.

Inorganic porous particle material used in the invention is ceramic hydroxyapatite.

The ceramic hydroxyapatite is characterized by having a range particle diameter size between 5–150 μm, preferably between 20–80 μm, a nominal pore diameter between 5–100 nm, preferably 50–100 nm, and a surface area between 40–50 m$^2$/g. Ceramic hydroxyapatite is commercially available from e.g. BIO-RAD Laboratories under trade name Macro-Prep®.

Loading of Porous Particles

The incorporation of the greasy, oily or sticky materials into the particles may be accomplished by conventional known methods. One is to dissolve the oil in suitable solvent and then mix with the porous particle material and dry. Alternatively the oil can be mixed directly with the porous particle materials. Another way is to use phase separation from a solution containing particles by addition of a non-solvent.

The porosity of the particles is 50–70% (v/v), preferably 62% (v/v).

When used in a drug delivery system the loaded porous particles may be used as such or filled into capsules, compressed to tablets or coated by ways well known in the art. The filling into capsules, compressing to tablets or coating should be performed in a manner that the fast release characteristics are not substantially changed. If fast release in the small intestine is desired, the loaded porous particles could be enteric coated.

WORKING EXAMPLES

Example 1

Hydroxyapatite Particles Containing Felodipine and 19.5% Cremophor® RH 40

The greasy/oily substance Cremophor® RH40 (312 mg) was melted at approx. 30° C. and used to dissolve felodipine (88 mg) in. The solution was poured on 1200 mg of hydroxyapatite particles having an average diameter of 80 μm (Macro Prep® Ceramic Hydroxyapatite; BIO-RAD Laboratories), under gentle manual mixing and mixing was continued until homogeneity.

The obtained particles were analyzed with regard to dissolution of felodipine using USP dissolution apparatus No. 2 (paddle), operated at 100 rpm. The dissolution medium used, having a temperature of 37 C., was phosphate buffer pH 6.5 containing 0.4 per cent of cetyltrimethylammonium bromide. The amount of felodipine released was determined by UV-spectrometry.

After 30 minutes the amount of felodipine dissolved was 84% (as average, n=2) of the found content.

Example 2

Hydroxyapatite Particles Containing Melagatran and 37% Akoline®

The greasy/oily substance Akoline® (779 mg) was melted at approx. 30° C. and used to dissolve melagatran (21 mg) in. The solution was poured on hydroxyapatite particles (1200 mg) having an average particle diameter of 80 μm (Macro Prep® Ceramic Hydroxyapatite; BIO-RAD Laboratories), under gentle mixing and mixing was continued until homogeneity.

The obtained particles were analyzed with regard to dissolution of Akoline® MCM and melagatran using a USP dissolution apparatus No. 2 (paddle), operated at 100 rpm. The dissolution medium used, having a temperature of 37° C., was phosphate buffer pH 6.8 with additions of 2 mM lecithin and 5 mM taurocholate to make the sample uptake homogenous. The sample components were separated by liquid chromatography. The amount of Akoline released was determined using a light scattering detector and the amount of melagatran released was determined by UV-spectrometry.

After 20 minutes the amount of Akoline® MCM dissolved was 71% (as average, n=2) of the found content. The amount of melagatran dissolved after 20 minutes was 94% (as average, n=2) of the found content.

Example 3

Hydroxyapatite Particles Containing 33.3% Almokalant

The oily/sticky substance almokalant (0.6 g, room temperatured) was poured on hydroxyapatite (1200 mg) particles having an average diameter of 80 μm (Macro Prep® Ceramic Hydroxyapatite; BIO-RAD Laboratories), under gentle manual mixing and mixing was continued until homogeneity.

The obtained particles were analyzed with regard to dissolution of almokalant using USP dissolution apparatous No.2 (paddle), operated at 100 rpm. The dissolution medium, used having a temperature of 37 C., was phosphate buffer pH 6.8. The amount of almokalant released was determined by UV-spectrometry.

After 30 minutes the amount of almokalant dissolved was 100% (as average, n=2) of the found content.

Example 4

Hydroxyapatite Particles Containing 17.4% Almokalant

The oily/sticky substance almokalant (0.35 g, room temperatured) was poured on hydroxyapatite (1.7 g) particles having an average diameter of 80 μm (Macro Prep® Ceramic Hydroxyapatite; BIO-RAD Laboratories), under gentle manual mixing and mixing was continued until homogeneity.

The obtained particles were analyzed with regard to dissolution of almokalant using USP dissolution apparatous No.2 (paddle), operated at 100 rpm. The dissolution medium, used having a temperature of 37 C., was phosphate buffer pH 6.8. The amount of almokalant released was determined by UV-spectrometry.

After 30 minutes the amount of almokalant dissolved was 80% (as average, n=2) of the found content.

Example 5

Particles obtained in example 1 were filled into hard gelatine capsules of size 3. Each capsule was filled with 190 mg of felodipine/hydroxyapatite particles.

What is claimed is:

1. An orally-administered dry, solid drug delivery composition which comprises:

a pharmaceutically active substance which is melagatran, and an absorption enhancer selected from the group consisting of a mono, di-, triglyceride or a mixture thereof, or a solubilizer selected from the group consisting of semi-solid and liquid non-ionic surface active agents, wherein the composition is in form of a plurality of porous inorganic particles composed of ceramic hydroxyapatite having a diameter of from 5 to 150 μm, said composition having fast release characteristics and incorporating from 15 wt % to 40 wt % of the pharmaceutically active substance and absorption enhancer or solubilizer.

2. An orally-administered dry, solid drug delivery composition which comprises a pharmaceutically active substance which is almokalant, wherein the composition is in form of a plurality of porous inorganic particles composed of ceramic hydroxyapatite having a diameter of from 5 to 150 μm, said composition having fast release characteristics and incorporating from 15 wt % to 40 wt % of the pharmaceutically active substance.

3. An oral dosage form comprising a dry, solid drug delivery composition, the composition comprising:

a thrombin inhibiting peptide drug having a molecular weight less than 1000 dalton, and an absorption enhancer selected from the group consisting of a mono, di-, triglyceride or a mixture thereof, or a solubilizer selected from the group consisting of semi-solid and liquid non-ionic surface active agents, wherein the composition is in the form of a plurality of porous inorganic particles composed of ceramic hydroxyapatite having a diameter of from 5 to 150 μm, said composition incorporating from 15 wt % to 40 wt % of the thrombin inhibiting peptide drug and the absorption enhancer or solubilizer, and wherein the composition is adapted to obtain a fast in vitro release of the pharmaceutically active substance corresponding to not less than 60% release of the pharmaceutically active substance within 30 minutes.

4. The oral dosage form according to claim 3, wherein the thrombin inhibiting peptide drug is melagatran.

5. An oral dosage form comprising a dry, solid drug delivery composition, the composition comprising: a pharmaceutically active substance which is felodipine, and an absorption enhancer selected from the group consisting of a mono, di-, triglyceride or a mixture thereof, or a solubilizer selected from the group consisting of semi-solid and liquid non-ionic surface active agents, wherein the composition is in the form of a plurality of porous inorganic particles composed of ceramic hydroxyapatite having a diameter of from 5 to 150 μm, said composition incorporating from 15 wt % to 40 wt % of the pharmaceutically active substance and the absorption enhancer or solubilizer, and wherein the composition is adapted to obtain a fast in vitro release of the pharmaceutically active substance corresponding to not less than 60% release of the pharmaceutically active substance within 30 minutes.

6. The oral dosage form according to any one of claim 1, 2, 3, or 5, wherein the ceramic hydroxyapatite has a diameter size of 20–80 μm.

7. The oral dosage form according to any one of claim 1, 2, 3, or 5, wherein the in vitro release is measured by a dissolution method employing a USP apparatus No. 2 equipped with a paddle a rotation speed of 100 rpm and a dissolution medium temperature of 37° C.

8. The oral dosage form according to any one of claims 3–5, wherein not less than 70% of the pharmaceutically active substance is released within 30 minutes.

9. The oral dosage form according to any one of claims 3–5, wherein not less than 80% of the pharmaceutically active substance is released within 30 minutes.

10. The oral dosage form according to claim 1, 2, 3, or 5, wherein the semi-solid or liquid non-ionic surface active solubilizer contains a polyethyleneglycol as an ester or ether.

11. The oral dosage form according to claim 10, wherein the polyethyleneglycol is a polyethoxylated fatty acid, hydroxylated fatty acid, or a fatty alcohol.

12. The oral dosage form according to claim 11, wherein the polyethyleneglycol is polyethoxylated castor oil, polyoxyethylenated hydrogenated castor oil, polyethoxylated fatty acid from castor oil, or polyethoxylated fatty acid from hydrogenated castor oil.

* * * * *

UNITED STATES PATENT AND TRADEMARK OFFICE
CERTIFICATE OF CORRECTION

PATENT NO.      : 6,558,703 B1
DATED           : May 6, 2003
INVENTOR(S)     : Karlsson et al.

It is certified that error appears in the above-identified patent and that said Letters Patent is hereby corrected as shown below:

Title page,
Item [56], References Cited, OTHER PUBLICATIONS, add:
-- File WPI, Derwent accession no. 94-299707, Kyoritsu Yogyo Genryo KK: "Controlled release pharmaceutic comprising self-curing calcium phosphate cement compsn. As supporting vehicle" --.

Column 6,
Lines 12 and 14 (2 instances): delete "claim" and substitute therefor -- claims --.
Line 18, insert -- , -- after "paddle".

Signed and Sealed this

Second Day of September, 2003

JAMES E. ROGAN
*Director of the United States Patent and Trademark Office*